United States Patent [19]

Oda et al.

[11] Patent Number: 5,409,957
[45] Date of Patent: Apr. 25, 1995

[54] PHENOXYALKYLAMINE AND AGRICULTURAL AND HORTICULTURAL BACTERICIDE

[75] Inventors: Mitsunori Oda; Kazutoshi Kikkawa; Akinori Tanaka; Satoko Imaruoka; Shigeo Yoshinaka, all of Niigata, Japan

[73] Assignee: Mitsubishi Gas Chemical Company, Inc., Tokyo, Japan

[21] Appl. No.: 35,903

[22] Filed: Mar. 23, 1993

Related U.S. Application Data

[63] Continuation of Ser. No. 617,577, Nov. 26, 1990, abandoned.

[30] Foreign Application Priority Data

Nov. 24, 1989 [JP] Japan .................... 1-303238

[51] Int. Cl.$^6$ .............. C07C 217/20; A01N 33/26
[52] U.S. Cl. .................... 514/651; 564/353; 564/354
[58] Field of Search ............ 564/353, 354; 514/651; 504/326

[56] References Cited

U.S. PATENT DOCUMENTS

| | | | |
|---|---|---|---|
| 2,952,678 | 9/1960 | Lane | 564/353 |
| 3,472,896 | 10/1969 | Seki et al. | 564/354 |
| 3,677,735 | 7/1972 | Richter et al. | 504/160 |
| 3,707,561 | 12/1972 | Sobel et al. | 564/354 |
| 3,729,511 | 4/1973 | Baker et al. | 564/353 |

FOREIGN PATENT DOCUMENTS 198311  10/1986  European Pat. Off. .

OTHER PUBLICATIONS

Blaha et al., Chem. Abs. 104:224693g (1986).

*Primary Examiner*—Glennon H. Hollrah
*Assistant Examiner*—Scott C. Rand
*Attorney, Agent, or Firm*—Sherman and Shalloway

[57] ABSTRACT

Disclosed are a phenoxyalkylamine represented by the following general formula I and a salt of said phenoxyalkylamine represented by the following general formula II:

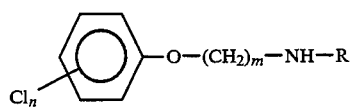

I and

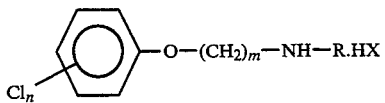

II wherein R represents a linear saturated hydrocarbon having 7 to 12 carbon atoms, n is an integer of from 1 to 5, m is an integer of from 2 to 4, and HX represents a mineral acid.

These compounds have strong bacteriostatic and bactericidal actions for plants with no phytotoxicity. Therefore, these compounds are effectively used as the active ingredient of an agricultural and horticultural bactericide.

8 Claims, No Drawings

PHENOXYALKYLAMINE AND AGRICULTURAL AND HORTICULTURAL BACTERICIDE

This application is a continuation of application Ser. No. 07/617,577, filed Nov. 26, 1990, now abandoned.

BACKGROUND OF THE INVENTION

1. Field of the Invention

The present invention relates to a novel phenoxyalkylamine and a salt thereof, and a novel agricultural and horticultural bactericide.

2. Description of the Related Art

Inorganic copper-containing agents, organic copper-containing agents and antibiotic agents such as streptomycin have been used as bactericides for phyto-pathogenic bacteria in agricultural plants.

However, these conventional bactericides are defective in that the effect is practically insufficient and the phytoxicity is caused. Accordingly, development of a bactericide having strong bacteriostatic and bactericidal actions (both of the actions will be collectively called "antibacterial action" hereinafter) and weaker phytotoxicity is desired at the present.

SUMMARY OF THE INVENTION

We made investigations with a view to solving the above problem of the conventional technique, and as the result, we discovered novel phenoxyalkylamines and salts thereof and we found that these compounds had bacteriostatic and bactericidal activities to phytopathogenic bacteria in agricultural and horticultural plants. The present invention has now been completed based on this finding.

More specifically, in accordance with one fundamental aspect of the present invention, there are provided a phenoxyalkylamine represented by the following general formula I and a salt of said phenoxyalkylamine represented by the following general formula II:

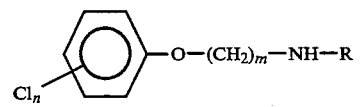
                                                    I

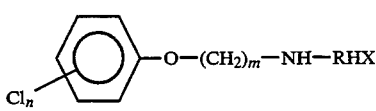
                                                    II wherein R represents a straight saturated hydrocarbon having 7 to 12 carbon atoms, n is an integer of from 1 to 5, m is an integer of from 2 to 4, and HX represents a mineral acid.

Furthermore, in accordance with the present invention, there is provided an agricultural and horticultural bactericide comprising the above-mentioned phenoxyalkylamine or salt thereof as an active ingredient.

DETAILED DESCRIPTION OF THE PREFERRED EMBODIMENTS

The phenoxyalkylamine of the present invention represented by general formula I is prepared, for example, by the following reactions:

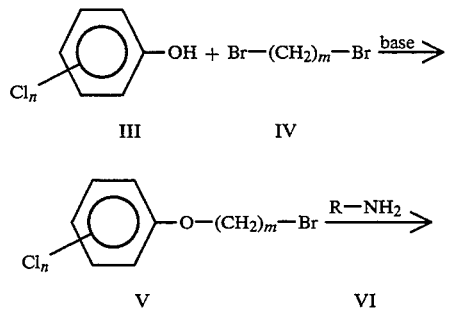

Namely, phenol III is reacted with dibromoalkane IV in the presence of a base such as sodium hydroxide in a solvent such as water, an alcohol, dimethylsulfoxide or dimethylformamide to give the compound V, which is then reacted with amine VI in the presence of a hydrogen bromide scavenger in a solvent such as an alcohol, dimethylsulfoxide or dimethylformamide to give the phenoxyalkylamine I of the present invention.

The phenoxyalkylamine salt of the present invention represented by general formula II is prepared, for example, by reacting the above-mentioned phenoxyalkylamine I with a mineral acid.

The mineral acid used is not particularly restricted and it can be used in either a gaseous or liquid state. As typical instances, there can be mentioned hydrochloric acid, hydrobromic acid, hydroiodic acid, sulfuric acid, nitric acid or phosphoric acid.

In general formula II, HX corresponds to the mineral acid used in the preparation.

In the preparation of salt II, use of a reaction solvent is not absolutely indispensable, but ordinarily a solvent is used. For example, an alcohol, ether or ester, or water can be used as a reaction solvent.

The reaction solvent is not particularly restricted. When a gaseous mineral acid is used, the loss of the gas can be reduced by lowering the reaction temperature down to 0° C. or lower.

The phenoxyalkylamine salt of the present invention is found to be solid at room temperature. It can be obtained from the reaction mixture by ordinary solid-liquid separation procedure such as filtration or centrifugation. If necessary, the covered crystals can be purified simply by washing with solvent or recrystallization from alcohol or water.

The physical properties of the phenoxyalkylamine represented by general formula I and the phenoxyalkylamine salt represented by general formula II are shown in Tables 1 and 2, respectively.

TABLE 1

Physical Properties of Phenoxyalkylamines

First Line: compound number $Cl_n$, m and R
Second and Subsequent Lines: 1 state, melting point and boiling point, 2 NMR δ values ppm $^1$H-NMR ($CDl_3$).

1. 2-CL, 2, $C_7H_{15}$—
   1 colorless oil, boiling point = 149~153° C./0.4 mmHg
   2 0.88(t-like, 3H), 1.32(m, 10H), 1.67(s, 1H), 2.68(t, J=6Hz, 2H), 3.02(t, J=5Hz, 2H), 4.11(t, J=5Hz, 2H), 6.7-7.5(m, 4H)
2. 2-Cl, 2 , $C_8H_{17}$—
   1 colorless oil, boiling point =152~158° C./0.5 mmHg
   2 0.89(t-like, 3H), 1.31(m, 12H), 1.72(s, 1H), 2.71(t, J=6Hz, 2H), 3.05(t, J=5Hz, 2H), 4.16(t, J=5Hz, 2H), 6.7-7.5(m, 4H)
3. 2-$Cl_2$, 2, $C_9H_{19}$—

TABLE 1-continued

Physical Properties of Phenoxyalkylamines 1 colorless oil, melting point(hydrochloride) = 195~197° C.
2 0.89(t-like, , 3H), 1.30(m, 14H), 1.70(s, 1H), 2.71(t, J=6Hz, 2H), 3.05(t, J=5Hz, 2H), 4.16(t, J=5Hz, 2H), 6.7-7.5(m, 4H)

4. 2-Cl, 2, C$_{10}$H$_{21}$—
1 colorless wax, boiling point = 162~165° C./0.4 mmHg
2 0.89(t-like, 3H), 1.28(m, 16H), 1.74(s, 1H), 2.71(t, J=6Hz, 2H), 3.05(t, J=5Hz, 2H), 4.15(t, J=5Hz, 2H), 6.7-7.5(m, 4H)

5. 2-Cl, 2, C$_{11}$H$_{23}$—
1 colorless oil, boiling point = 166~169° C./0.3 mmHg
2 0.88(t, J=6Hz, 3H), 1.26(br, 18H), 1.88(s, 1H), 2.67(t, J=6Hz, 2H), 3.00(t, J=5Hz, 2H), 4.08(t, J=5Hz, 2H), 6.6-7.4(m, 4H)

6. 2-Cl, 2, C$_{12}$H$_{25}$—
1 colorless oil, boiling points = 170~175° C./0.1 mmHg
2 0.88 (t, J=6Hz, 3H), 1.26(br, 18H), 1.88(s, 1H), 2.68 (t, J=6Hz, 2H), 3.02(t, J=5Hz, 2H), 41.1(t, J=5Hz, 2H), 6.7-7.4(m, 4H)

7. 3-Cl, 2 , C$_7$H$_{15}$—
1 colorless oil, boiling point = 149~152° C./0.5 mmHg
2 0.87(t-like, 3H), 1.31(m, 10H), 1.66(s, 1H), 2.65(t, J=6Hz, 2H), 2.96(t, J=5Hz, 2H), 4.01(t, J=5Hz, 2H), 6.6-7.2(m, 4H)

8. 3-Cl, 2, C$_8$H$_{17}$—
1 colorless oil, boiling point = 148~150° C./0.2 mmHg
2 0.89(t-like, 3H), 1.34(m, 12H), 1.68(s, 1H) 2.45(t, J=6Hz, 2H), 2.99(t, J=5Hz, 2H), 4.05(t, J=5Hz, 2H), 6.7-7.5(m, 4H)

9. 3-Cl, 2, C$_9$H$_{19}$—
1 colorless oil, boiling point = 149~155° C./0.2 mmHg
2 0.89(t-like, 3H), 1.35(m, 16H), 1.48(s, 1H), 2.46(t, J=6Hz, 2H), 2.98(t, J=5Hz, 2H), 4.06(t, J=5Hz, 2H), 6.7-7.5(m, 4H)

10. 3-Cl, 2, C$_{10}$H$_{21}$—
1 colorless oil, boiling point = 150~159° C./0.2 mmHg
2 0.87(t-like, 3H), 1.26(m, 16H), 1.52(s, 1H), 2.65(t, J=6Hz, 2H), 2.97(t, J=5Hz, 2H), 4.03(t, J=5Hz, 2H), 6.7-7.5(m, 4H)

11. 4-Cl, 2, C$_7$H$_{15}$—
1 colorless oil, melting point (hydrochloride) = 215~218° C.
2 0.88(t-like, 3H), 1.30(m, 10H), 1.58(s, 1H), 2.67(t, J=6Hz, 2H), 2.98(t, J=5Hz, 2H), 4.02(t, J=5Hz, 2H), 6.80(d, J=8Hz, 2H) 7.20(d, J=8Hz, 2H)

12. 4-Cl, 2, C$_8$H$_{17}$—
1 colorless oil, melting point (hydrochloride) = 210~212° C.
2 0.88(t-like, 3H), 1.29(m, 12H), 1.57(s, 1H), 2.64(t, J=6Hz, 2H), 2.95(t, J=5Hz, 2H), 4.00(t, J=5Hz, 2H), 6.74(d, J=8Hz, 2H) 7.19(d, J=8Hz, 2H)

13. 4-Cl, 2, C$_9$H$_{19}$—
1 colorless oil, melting point (hydrochloride) = 208~210° C.
2 0.89(t-like, 3H), 1.29(m, 14H), 1.61(s, 1H), 2.65(t, J=6Hz, 2H), 2.96(t, J=5Hz, 2H), 4.00(t, J=5Hz, 2H), 6.75(d, J=8Hz, 2H) 7.17(d, J=8Hz, 2H)

14. 4-Cl, 2, C$_{10}$H$_{21}$—
1 colorless oil, melting point (hydrochloride) = 209~212° C.
2 0.88(t-like, 3H), 1.26(m, 16H), 1.65(s, 1H), 2.63(t, J=6Hz, 2H), 2.95(t, J=5Hz, 2H), 4.00(t, J=5Hz, 2H), 6.76(d, J=9Hz, 2H) 7.17(d, J=9Hz, 2H)

15. 4-Cl, 2, C$_{11}$H$_{23}$—
1 colorless oil, melting point (hydrochloride) = 207~212° C.
0.88(t-like, 3H), 1.26(m, 18H), 1.69(s, 1H), 2.65(t, J=6Hz, 2H), 2.97(t, J=5Hz, 2H), 4.01(t, J=5Hz, 2H), 6.76(d, J=9Hz, 2H) 7.17(d, J=9Hz, 2H)

16. 4-Cl, 2, C$_{12}$H$_{25}$—
1 colorless needle, melting point (hydrochloride) = 32~34° C.
2 0.88(t, J=6Hz, 3H), 1.26(m, 20H), 1.54(s, 1H), 2.65(t, J=6Hz, 2H), 2.97(t, J=5Hz, 2H), 4.01(t, J=5Hz, 2H), 6.79(d, J=9Hz, 2H) 7.18(d, J=9Hz, 2H)

17. 2,3-Cl$_2$, 2, C$_7$H$_{15}$—
1 colorless oil, boiling point = 160~167° C./0.4 mmHg
2 0.88(t-like, 3H), 1.33(m, 10H), 1.63(s, 1H), 2.68(t-like, 2H), 3.03(t, J=5Hz, 2H), 4.11(t, J=5Hz, 2H), 6.6-7.2(m, 3H)

18. 2,3-Cl$_2$, 2, C$_8$H$_{17}$—
1 colorless oil, boiling point = 175~178° C./0.3 mmHg
2 0.87(t-like, 3H), 1.29(m, 12H), 1.64(s, 1H), 2.67(t-like, 2H), 3.01(t, J=5Hz, 2H), 4.09(t, J=5Hz, 2H), 6.7-7.1(m, 3H)

19. 2,3-Cl$_2$, 2, C$_9$H$_{19}$—
1 colorless oil, boiling point = 176~181°C./0.2 mmHg
2 0.87(t-like, 3H), 1.27(m, 14H), 1.66(s, 1H), 2.67(t-like, 2H), 3.01(t, J=5Hz, 2H), 4.08(t, J=5Hz, 2H), 6.6-7.1(m, 3H)

20. 2,3-Cl$_2$, 2, C$_{10}$H$_{21}$—
1 colorless oil, boiling point = 178~182° C./0.1 mmHg
2 0.87(t-like, 3H), 1.26(m, 16H), 1.61(s, 1H), 2.66(t-like, 2H), 3.01(t, J=5Hz, 2H), 4.10(t, J=5Hz, 2H), 6.6-7.2(m, 3H)

21. 2,4-Cl$_2$, 2, C$_7$H$_{15}$—
1 colorless oil, boiling point = 168~171° C./0.2 mmHg
2 0.88(t-like, 3H), 1.33(m, 10H) 1.61(s, 1H), 2.68(t-like, 2H), 3.02(t, J=5Hz, 2H), 4.10(t, J=5Hz, 2H), 6.83(d, J=9Hz, 1H), 7.15(dd, J=9, 2Hz, 1H), 7.33(d, J=2Hz, 1H)

22. 2,4- Cl$_2$, 2, C$_8$H$_{17}$—
1 colorless oil, boiling point = 170~174° C./0.2 mmHg
2 0.87(t-like, 3H), 1.30(m, 12H), 1.80(s, 1H), 2.69(t-like, 2H), 3.02(t, J=5Hz, 2H), 4.10(t, J=5Hz, 2H), 6.83(d, J=2Hz, 1H), 7.17(dd, J=8, 2Hz, 1H), 7.32(d, J=2Hz, 1H)

23 2,4-Cl$_2$, 2, C$_9$H$_{19}$—
1 colorless oil, boiling point = 173~178° C./0.2 mmHg
2 0.88(t-like, 3H), 1.29(m, 14H), 1.63(s, 1H), 2.69(t-like, 2H), 3.03(t, J=5Hz, 2H), 4.11(t, J=5Hz, 2H), 6.83(d, J=9Hz, 1H), 7.18(dd, J=9, 2Hz, 1H), 7.36(d, J=2Hz, 1H)

24 2,4-Cl$_2$, 2, C$_{10}$H$_{21}$—
1 colorless oil, boiling point = 180~185° C./0.2 mmHg
2 0.90(t-like, 3H), 1.27(m, 16H), 1.73(s, 1H), 2.67(t-like, 2H), 3.01(t, J=5Hz, 2H), 4.08(t, J=5Hz, 2H), 6.78(d, J=8Hz, 1H) 7.12(dd, J=8, 2Hz, 1H), 7.30(d, J=2Hz, 1H)

25. 2,4-Cl$_2$, 2, C$_{12}$H$_{25}$—
1 colorless plate, melting point = 34~36° C.
2 0.86(t-like, 3H), 1.25(m, 20H), 1.66(s, 1H), 2.66(t-like, 2H), 2.99(t, J=5Hz, 2H), 4.07(t, J=5Hz, 2H), 6.76(d, J=9Hz, 2H) 7.10(dd, J=9, 2Hz, 1H), 7.26(d, J=2Hz, 1H)

26. 2,4-Cl$_2$, 3, C$_7$H$_{15}$—
1 colorless oil, melting point(hydrochloride) = 185~188° C.
2 0.88(t, J=5Hz, 3H), 1.30(m, 10H), 1.37(s, 1H), 1.98(pen, J=6Hz, 2H), 2.62(t, J=5Hz, 2H), 2.82(t, J=6Hz, 2H), 4.06(t, J=6Hz, 2H) 6.78(d, J=9Hz, 1H), 7.13(dd, J=9, 2Hz, 1H), 7.30(d, J=2Hz, 1H)

27. 2,4-Cl$_2$, 3, C$_8$H$_{17}$—
1 colorless oil, melting point (hydrochloride) = 180~183° C.
2 0.88(t, J=5Hz, 3H), 1.27(m, 12H), 1.33(s, 1H), 2.00(pen, J=6Hz, 2H), 2.62(t, J=5Hz, 2H), 2.83(t, J=6Hz, 2H), 4.06(t, J=6Hz, 2H) 6.78(d, J=9Hz, 1H), 7.14(dd, J=9, 2Hz, 1H), 7.30(d, J=2Hz, 1H)

28. 2,4-Cl$_2$, 3, C$_9$H$_{19}$—
1 colorless oil, melting point (hydrochloride) = 177~180° C.
2 0.88(t, J=5Hz, 3H), 1.26(m, 14H), 1.58(s, 1H), 2.00(pen, J=6Hz, 2H), 2.63(t, J=5Hz, 2H), 2.83(t, J=6Hz, 2H), 4.07(t, J=6Hz, 2H) 6.80(d, J=9Hz, 1H), 7.16(dd, J=9, 2Hz, 1H), 7.33 (d, J=2Hz, 1H)

29. 2,4-Cl$_2$, 3, C$_{10}$H$_{21}$—
1 colorless oil, melting point (hydrochloride) = 175~177° C.
2 0.87(t, J=4Hz, 3H), 1.27(m, 17H), 1.98(pen, J=6Hz, 2H), 2.62(t, J=5Hz, 2H), 2.83(t, J=6Hz, 2H), 4.07(t, J=6Hz, 2H)

TABLE 1-continued

Physical Properties of Phenoxyalkylamines 6.80(d, J=9Hz, 1H), 7.16(dd, J=9, 2Hz, 1H)
      7.33(d, J=2Hz, 1H)
30. 2,4-Cl$_2$, 4, C$_7$H$_{15}$—
  1  colorless oil, melting point (hydrochloride) = 171~173° C.
  2  0.88(t, J=5Hz, 3H), 1.31(m, 10H), 1.71(s, 1H), 1.80(m, 4H), 2.59(t, J=6Hz, 2H), 2.68(t, J=6Hz, 2H), 3.98(t, J=6Hz, 2H) 6.73(d, J=9Hz, 1H), 7.08(dd, J=9, 2Hz, 1H) 7.26(d, J=2Hz, 1H)
31. 2,4-Cl$_2$, 4, C$_8$H$_{17}$—
  1  colorless prism, melting point (hydrochloride) = 32~33° C.
  2  0.87(t, J=5Hz, 3H), 1.29(m, 12H), 1.51(s, 1H), 1.80(m, 4H), 2.58(t, J=6Hz, 2H), 2.67(t, J=6Hz, 2H), 3.96(t, J=6Hz, 2H) 6.73(d, J=9Hz, 1H), 7.06(dd, J=9, 2Hz, 1H) 7.26(d, J=2Hz, 1H)
32. 2,4-Cl$_2$, 4, C$_9$H$_{19}$—
  1  colorless oil, melting point (hydrochloride) = 185~188° C.
  2  0.87(t, J=5Hz, 3H), 1.27(m, 14H), 1.61(s, 1H), 1.80(m, 4H), 2.59(t, J=6Hz, 2H), 2.67(t, J=6Hz, 2H), 3.98(t, J=6Hz, 2H) 6.74(d, J=9Hz, 1H), 7.10(dd, J=9, 2Hz, 1H) 7.30(d, J=2Hz, 1H)
33. 2,4-Cl$_2$, 4, C$_{10}$H$_{21}$—
  1  colorless scale, melting point = 39~40° C.
  2  0.88(t, J=5Hz, 3H), 1.26(m, 17H), 1.80(m, 4H), 2.58(t, J=6Hz, 2H), 2.67(t, J=6Hz, 2H), 3.98(t, J=6Hz, 2H), 6.74(d, J=9Hz, 2H) 7.10(dd, J=9, 2Hz, 1H), 7.30(d, J=2Hz, 1H)
34. 2,5-Cl$_2$, 2, C$_7$H$_{15}$—
  1  colorless oil, boiling point = 180~184° C./0.2 mmHg
  2  0.87(t-like, 3H), 1.32(m, 10H), 1.55(s, 1H), 2.67(t-like, 2H), 3.01(t, J=5Hz, 2H), 4.07(t, J=5Hz, 2H), 6.7-7.3(m, 3H)
35. 2,5-Cl$_2$, 2, C$_8$H$_{17}$—
  1  colorless oil, boiling point = 183~188° C./0.2 mmHg
  2  0.89(t-like, 3H), 1.29(m, 12H), 1.56(s, 1H), 2.67(t-like, 2H), 3.02(t, J=5Hz, 2H), 4.12(t, J=5Hz, 2H), 6.7-7.4(m, 3H)
36. 2,5-Cl$_2$, 2, C$_9$H$_{19}$—
  1  colorless oil, boiling point = 190~195° C./0.2 mmHg
  2  0.88(t-like, 3H), 1.28(m, 14H), 1.55(s, 1H), 2.66(t-like, 2H), 3.01(t, J=5Hz, 2H), 4.08(t, J=5Hz, 2H), 6.7-7.3(m, 3H)
37. 2,5-Cl$_2$, 2, C$_{10}$H$_{21}$—
  1  colorless oil, boiling point = 190~192° C./0.1 mmHg
  2  0.89(t-like, 3H), 1.29(m, 16H), 1.39(s, 1H), 2.72(t-like, 2H), 3.03(t, J=5Hz, 2H), 4.10(t, J=5Hz, 2H), 6.7-7.3(m, 3H)
38. 2,6-Cl$_2$, 2, C$_7$H$_{15}$—
  1  colorless oil, boiling point = 180~185° C./0.3 mmHg
  2  0.89(t-like, 3H), 1.33(m, 10H), 1.81(s, 1H), 2.70(t-like, 2H), 3.02(t, J=5Hz, 2H), 4.16(t, J=5Hz, 2H), 6.7-7.3(m, 3H)
39. 2,6-Cl$_2$, 2, C$_8$H$_{17}$—
  1  colorless oil, boiling point = 187~190° C./0.3 mmHg
  2  0.87(t-like, 3H), 1.32(m, 10H), 1.82(s, 1H), 2.69(t-like, 2H), 3.02(t, J=5Hz, 2H), 4.15(t, J=5Hz, 2H), 6.7-7.3(m, 3H)
40. 2,6-Cl$_2$, 2, C$_9$H$_{19}$—
  1  colorless oil, boiling point = 180~183° C./0.1 mmHg
  2  0.85(t-like, 3H), 1.30(m, 15H), 2.71(t-like, 2H), 3.04(t, J=5Hz, 2H), 4.17(t, J=5Hz, 2H), 6.7-7.3(m, 3H)
41. 2,6-Cl$_2$, 2, C$_{10}$H$_{21}$—
  1  colorless oil, boiling point = 180~185° C./0.08 mmHg
  2  0.88(t-like, 3H), 1.26(m, 16H), 1.76(s, 1H), 2.72(t-like, 2H), 3.05(t, J=5Hz, 2H), 4.20(t, J=5Hz, 2H), 6.7-7.4(m, 3H)
42. 2,6-Cl$_2$, 2, C$_{11}$H$_{23}$—
  1  colorless oil, boiling point = 180~188° C./0.06 mmHg
  2  0.87(t-like, 3H), 1.27(m, 18H), 1.78(s, 1H), 2.68(t-like, 2H), 3.01(t, J=5Hz, 2H), 4.15(t, J=5Hz, 2H), 6.7-7.3(m, 3H)
43. 2,6-Cl$_2$, 2, C$_{12}$H$_{25}$—
  1  colorless oil, boiling point = 185~190° C./0.06 mmHg
  2  0.86(t-like, 3H), 1.25(m, 20H), 1.61(s, 1H), 2.67(t-like, 2H), 3.00(t, J=5Hz, 2H), 4.14(t, J=5Hz, 2H), 6.7-7.3(m, 3H)
44. 3, 4-Cl$_2$, 2, C$_7$H$_{15}$—
  1  colorless oil, boiling point = 170~174° C./0.2 mmHg
  2  0.88(t-like, 3H), 1.30(m, 10H), 1.54(s, 1H), 2.65(t-like, 2H), 2.97(t, J=5Hz, 2H), 3.98(t, J=5Hz, 2H), 6.65(dd, J=8, 3Hz, 1H), 6.90(d, J=3Hz, 1H), 7.24(d, J=8Hz, 1H)
45. 3, 4-Cl$_2$, 2, C$_8$H$_{17}$—
  1  colorless oil, boiling point = 172~177° C./0.2 mmHg
  2  0.88(t-like, 3H), 1.30(m, 10H) 2.65(t-like, 2H), 2.96(t, J=5Hz, 2H), 4.02(t, J=5Hz, 2H), 6.71(dd, J=8, 3Hz, 1H), 6.96(d, J=3Hz, 1H), 7.28(d, J=8Hz, 1H)
46. 3, 4-Cl$_2$, 2, C$_9$H$_{19}$—
  1  colorless oil, boiling point = 180~183° C./0.2 mmHg
  2  0.87(t-like, 3H), 1.30(m, 14H), 1.60(s, 1H), 2.65(t-like, 2H), 2.97(t, J=5Hz, 2H), 4.01(t, J=5Hz, 2H), 6.69(dd, J=8, 3Hz, 1H), 6.95(d, J=3Hz, 1H), 7.25(d, J=8Hz, 1H)
47. 3, 4-Cl$_2$, 2, C$_{10}$H$_{21}$—
  1  colorless oil, boiling point = 182~184° C./0.6 mmHg
  2  0.87(t-like, 3H), 1.27(m, 16H), 1.56(s, 1H), 2.65(t-like, 2H), 2.97(t, J=5Hz, 2H), 4.01(t, J=5Hz, 2H), 6.87(dd, J=8, 3Hz, 1H), 6.96(d, J=3Hz, 1H), 7.28(d, J=8Hz, 1H)
48. 3,5-Cl$_2$, 2, C$_7$H$_{15}$—
  1  colorless oil, boiling point = 160~165° C./0.2 mmHg
  2  0.88(t-like, 3H), 1.33(m, 11H), 2.66(t-like, 2H), 2.98(t, J=5Hz, 2H), 4.03(t, J=5Hz, 2H), 6.78(d, J=2Hz, 2H), 6.92(t, J=2Hz, 1H)
49. 3,5-Cl$_2$, 2, C$_8$H$_{17}$—
  1  colorless oil, boiling point = 168~170° C./0.1 mmHg
  2  0.88(t-like, 3H), 1.30(m, 12H), 1.47(s, 1H), 2.65(t-like, 2H), 2.97(t, J=5Hz, 2H), 4.02(t, J=5Hz, 2H), 6.77(d, J=1Hz, 2H), 6.90(t, J=1Hz, 1H),
50. 3,5-Cl$_2$, 2, C$_9$H$_{19}$—
  1  colorless oil, boiling point = 170~175° C./0.1 mmHg
  2  0.87(t-like, 3H), 1.28(m, 14H), 1.46(s, 1H), 2.68(t-like, 2H), 2.97(t, J=5Hz, 2H), 4.00(t, J=5Hz, 2H), 6.74(d, J=2Hz, 1H), 6.89(t, J=2Hz, 1H),
51. 3,5-Cl$_2$, 2, C$_{10}$H$_{20}$—
  1  colorless oil, boiling point = 170~173° C./0.06 mmHg
  2  0.89(t-like, 3H), 1.28(m, 16H), 1.47(s, 1H), 2.67(t=6Hz, 2H), 2.98(t, J=5Hz, 2H), 4.02(t, J=5Hz, 2H), 6.74(d, J=1Hz, 2H), 6.89(t, J=1Hz, 1H),
52. 2,4,5-Cl$_3$, 2, C$_7$H$_{15}$—
  1  colorless oil, melting point(hydrochloride) =158~160° C.
  2  0.88(t-like, 3H), 1.32(m, 10H), 1.55(s, 1H), 2.68(t-like, 2H), 3.03(t, J=5Hz, 2H), 4.08(t, J=5Hz, 2H), 6.96(s, 1H), 7.37(s, 1H)
53. 2,4,5-Cl$_3$, 2, C$_8$H$_{17}$—
  1  colorless oil, melting point(hydrochloride) = 154~156° C.
  2  0.88(t-like, 3H), 1.30(m, 12H), 1.60(s, 1H), 2.69(t, J=5Hz, 2H), 3.02(t, J=5Hz, 2H), 4.10(t, J=5Hz, 2H), 6.98(s, 1H), 7.40(s, 1H),
54. 2,4,5-Cl$_3$, 2, C$_9$H$_{17}$—
  1  colorless plate, melting point =29~30° C.
  2  0.88(t-like, 3H), 1.28(m, 14H), 1.52(s, 1H), 2.66(t-like, 2H), 3.01(t, J=5Hz, 2H), 4.06(t, J=5Hz, 2H), 6.91(s, 1H), 7.32(s, 1H),
55. 2,4,5-Cl$_3$, 2, C$_{10}$H$_{21}$—
  1  colorless plate, melting point =30~32° C.
  2  0.88(t-like, 3H), 1.27(m, 14H), 1.55(s, 1H), 2.67(t-like, 2H), 3.02(t, J=5Hz, 2H), 4.09(t, J=5Hz, 2H), 6.95(s, 1H), 7.37(s, 1H),
56. 2,4,6-Cl$_2$, 2, C$_7$H$_{15}$—
  1  colorless oil, melting point(hydrochloride) = 175~176° C.
  2  0.88(t-like, 3H), 1.34(m, 10H), 1.68(s, 1H), 2.69(t-like, J=6Hz, 2H), 3.02(t, J=6Hz, 2H), 4.14(t, J=6Hz, 2H), 7.28(s, 2H),
57. 2,4,6- Cl$_3$, 2, C$_8$H$_{17}$—
  1  colorless oil, boiling point =182~185° C/0.05 mmHg
  2  0.89(t-like, 3H), 1.31(m, 12H), 1.68(s, 1H), 2.68(t-like, 2H), 3.01(t, J=6Hz, 2H),

TABLE 1-continued

Physical Properties of Phenoxyalkylamines 4.13(t, J=6Hz, 2H), 7.24(s, 2H),
58. 2,4,6-Cl$_3$, 2, C$_9$H$_{19}$—
 1  colorless oil, boiling point =183~185° C./0.05 mmHg
 2  0.90(t-like, 3H), 1.30(m, 14H), 1.71(s, 1H),
    2.70(t-like, J=6Hz, 2H), 3.03(t, J=5Hz, 2H),
    4.15(t, J=5Hz, 2H), 7.25(s, 2H),
59. 2,4,6-Cl$_3$, 2, C$_{10}$H$_{21}$—
 1  colorless oil, melting point(hydrochloride) =
    159~160° C.
 2  0.87(t-like, 3H), 1.27(m, 16H), 1.66(s, 1H),
    2.68(t-like, J=6Hz, 2H), 3.00(t, J=5Hz, 2H),
    4.11(t, J=5Hz, 2H), 7.22(s, 2H),
60. 2,3,4,5,6-Cl$_5$, 2, C$_8$H$_{17}$—
 1  colorless oil, melting point(hydrochloride) =
    202~203° C.
 2  0.87(t-like, 3H), 1.31(m, 12H), 1.60(s, 1H),
    2.66(t, J=6Hz, 2H), 3.05(t, J=5Hz, 2H),
    4.13(t, J=5Hz, 2H),

TABLE 2

Physical Property of Phenoxyalkylamine Salts

| Compound No. | Cl$_n$ | m | R | HX | m.p. (°C.) |
|---|---|---|---|---|---|
| 61 | 4-Cl | 2 | C$_9$H$_{19}$— | HCl | 208~210 |
| 62 | 4-Cl | 2 | C$_{10}$H$_{21}$— | HCl | 209~212 |
| 63 | 4-Cl | 2 | C$_{11}$H$_{23}$— | HCl | 207~212 |
| 64 | 4-Cl | 2 | C$_{12}$H$_{25}$— | HCl | 206~211 |
| 65 | 2,3-Cl$_2$ | 2 | C$_8$H$_{17}$— | HCl | 158~160 |
| 66 | 2,4-Cl$_2$ | 2 | C$_8$H$_{17}$— | HCl | 191~193 |
| 67 | 2,4-Cl$_2$ | 2 | C$_7$H$_{15}$— | HCl | 171~173 |
| 68 | 2,4-Cl$_2$ | 2 | C$_8$H$_{17}$— | HCl | 164~168 |
| 69 | 2,4-Cl$_2$ | 2 | C$_9$H$_{19}$— | HCl | 160~162 |
| 70 | 2,4-Cl$_2$ | 2 | C$_{10}$H$_{21}$— | HCl | 151~153 |
| 71 | 2,4-Cl$_2$ | 2 | C$_8$H$_{17}$— | HCl | 180~183 |
| 72 | 2,4-Cl$_2$ | 2 | C$_9$H$_{19}$— | HCl | 177~180 |
| 73 | 2,4-Cl$_2$ | 3 | C$_{10}$H$_{21}$— | HCl | 175~177 |
| 74 | 2,4-Cl$_2$ | 4 | C$_7$H$_{15}$— | HCl | 171~173 |
| 75 | 2,4-Cl$_2$ | 4 | C$_8$H$_{17}$— | HCl | 180~183 |
| 76 | 2,4-Cl$_2$ | 4 | C$_9$H$_{19}$— | HCl | 185~188 |
| 77 | 2,4-Cl$_2$ | 4 | C$_{10}$H$_{21}$— | HCl | 180~183 |
| 78 | 2,4,5-Cl$_2$ | 2 | C$_8$H$_{17}$— | HCl | 154~156 |
| 79 | 2,3,4,5,6-Cl$_2$ | 2 | C$_8$H$_{17}$— | HCl | 202~203 |
| 80 | 2,4-Cl$_2$ | 2 | C$_8$H$_{17}$— | HBr | 180~183 |
| 81 | 2,4-Cl$_2$ | 2 | C$_8$H$_{17}$— | HI | 153~156 |
| 82 | 2,4-Cl$_2$ | 2 | C$_8$H$_{17}$— | HNO$_3$ | 107~108 |
| 83 | 2,4-Cl$_2$ | 2 | C$_8$H$_{17}$— | H$_3$PO$_1$ | 115~116 |

In accordance with another fundamental aspect of the present invention, there is provided an agricultural and horticultural bactericide which comprises as an active ingredient at least one member selected from the group consisting of phenoxyalkylamines represented by the following general formula I and salts of said phenyloxyalkylamines represented by the following general formula II:

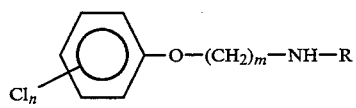

I and

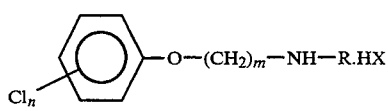

II wherein R represents a straight saturated hydrocarbon having 7 to 12 carbon atoms, n is an integer of from 1 to 5, m is an integer of from 2 to 4, and HX represents a mineral acid.

The phenoxyalkylamine represented by general formula I and the phenoxyalkylamine salt represented by general formula II (collectively expressed as the "phenoxyalkylamines" hereinafter) have strong bacteriostatic and bactericidal actions to bacteria such as, *Erwinia cartovera* and to bacteria belonging to the genus Xanthomonas such as bacteria causing citrus canker and bacteria belonging to the genus Corynebacterium such as bacteria causing tomato canker, and also to bacteria causing blights in agricultural and horticulture plants.

Each of the phenoxyalkylamines is chemically stable and can be preserved for a long time.

Accordingly, because of the strong bacteriostatic and bactericidal actions and the good stability characteristics of the phenoxyalkylamines as the active ingredient, the agricultural and horticultural bactericide of the present invention has a very high practical utility.

Each of the phenoxyalkylamines used as an active ingredient of the agricultural and horticultural bactericide of the present invention has a broad antibacterial spectrum, and therefore, the agricultural and horticultural bactericide of the present invention is effective for controlling a variety of diseases caused by various pathogenic bacteria, such as citrus canker, bacterial leaf blight of rice, bacterial shot hole of peach, black rot of cabbage, bacterial blight of lettuce, bacterial spot of melon, leaf blight of soy bean, tomato canker and soft rot of Chinese cabbage.

The phenoxyalkylamine salt is advantageous over the phenoxyalkylamine as an active ingredient of the agricultural bactericide of the present invention because the antibacterial action is stronger, the stability is higher and the risk of the phytoxicity is lower.

The agricultural and horticultural bactericide of the present invention can be formed into an optional preparation of an agricultural and horticultural agent, especially a bactericide, such as a wettable powder, a liquid, an emulsifiable concentrate, a flowable (sol) preparation, a powder, a driftless (DL) dust or a granule by using the novel compound of the present invention according to customary procedures.

The carrier to be used for such preparations is not particularly restricted, and any of carriers customarily used in this field can be used.

As typical instances of the solid carrier, there can be mentioned mineral powders such as kaolin, bentonite, clay, talc and vermiculite, plant powders such as wood meal, starch and crystalline cellulose, and polymeric compounds such as a petroleum resin, polyvinyl chloride, a ketone resin and dammar gum. As typical instances of the liquid carrier, there can be mentioned water, alcohols such as methyl alcohol, ethyl alcohol, n-propyl alcohol, isopropyl alcohol, butanol, ethylene glycol and benzyl alcohol, aromatic hydrocarbons such as toluene, benzene, xylene, ethylenebenzene and methylphthalene, halogenated hydrocarbons such as chloroform, carbon tetrachloride, dichloromethane, chloroethylene, monochlorobenzene, trichlorofluoromethane and dichlorofluoromethane, ethers such as ethyl ether, ethylene oxide and dioxane, ketones such as acetone, methylethylketone, cyclohexanone and methylisobutylketone, esters such as ethyl acetate, butyl acetate and ethylene glycol acetate, acid amides such as dimethylformamide and dimethylacetamide, sulfoxides such as dimethylsulfoxide, alcoholic ethers, such as ethylene glycol, monomethyl ether and ethylene glycol monoethyl ether, aliphatic and alicyclic hydrocarbons such as n-hexane and cyclohexane, gasolines of the industrial grade such as petroleum ether and solvent naphtha, paraffins, and petroleum fractions such as kerosene and gas oil.

Various surface-active agents can be used. As typical instances of the surface-active agent, there can be mentioned nonionic surface-active agents such as polyoxyethylene alkyl ether and polyoxyethylene alkyl ether and polyoxyethylene alkyl ester, anionic surface-active agents such as alkyl benzenesulfonate and alkyl sulfate, cationic surface active agents such as lauryl and sterytrimethyl ammonium chlorides, and amphoteric surface active agents such as betaine-type carboxylic acid and sulfuric acid esters.

The content of the ingredient of the present invention in preparation as mentioned above is not particularly restricted, but from the practical viewpoint, it is generally about 0.001 to about 95% by weight (expressed as the compound of general formula I; the same will apply hereinafter) and preferably about 0.1 to about 90% by weight. Practically, in case of a powder, a DL, dust and a granule, the content of the compound of the present invention is about 0.01 to about 5% by weight, and in case of wettable powder, a concentrate and an emulsifiable liquid, the content of the compound of the present invention is about 1 to about 75% by weight.

The so-formed preparation, for example, a powder, a driftless dust or a granule, is directly applied, and a wettable powder, a concentrate, an emulsifiable liquid or a flowable agent is applied after it has been diluted with water or an appropriate solvent.

The agricultural and horticultural agent of the present invention can be used in combination with other agricultural horticultural bactericides, fungicides, herbicides, insecticides and plant growth regulators and also with fertilizers.

The agricultural and horticultural bactericide of the present invention is directly or after dilution scattered on leaves or stems of plants or onto the water surface, into water, to the soil surface or into the interior of the soil.

The application rate of the agricultural and horticultural bactericide of the present invention depends on the kind of the objective disease, the degree of the disease, the kind of plant, the application location, the application method and the kind of preparation, and it is difficult to specify the application rate simply. However, in case of a powder, driftless dust or granule (the concentration of the active ingredient is 3% by weight), the applied amount is 2 to 6 kg per 10 ares. In case of a wettable powder, liquid, emulsifiable concentrate or flowable agent (the concentration of the active ingredient is 20% by weight), 0.05 to 3 kg of the active component is used in the state diluted with 100 to 500 l of water per 100 ares.

The compound of the present invention, especially the compound represented by general formula II, has a strong antibacterial action, a high stability and no risk of the phytoxicity, and therefore, the application range is broad and the compound of the present invention can be used for not only curing but also preventing disease in cultivation plants.

The present invention will now be described in detail with reference to the following examples that by no means limit the scope of the invention.

EXAMPLE 1

Synthesis of
N-2-(2,4-dichlorophenoxy)ethyl-N-n-octylamine
(compound No. 22)

In 20 ml of ethanol was dissolved 2.70 g (10.0 millimoles) of 2-(2,4-dichlorophenoxy)ethyl bromide, and 1.06 g (10.0 millimoles) of anhydrous sodium carbonate and 3.87 g (30.0 millimoles) of n-octylamine were added to the solution. The mixture was refluxed for 6 hours on an oil bath. After cooling, the reaction mixture was poured into 100 ml of water and extracted with 20 ml of chloroform three times.

The organic layer was dried over magnesium sulfate and the solvent was removed by distillation, and the residue was purified by silica gel column chromatography (eluent: ethanol/chloroform=4/9) to give 2.67 g (84% yield) of compound No. 22 in the form of a colorless oil.

The physical properties of the obtained compound were as follows.

$^{13}$C-NMR (CDCL$_3$): 14.03(q), 22.62(t), 27.26(t), 29.24(t), 29.48(t), 30.09(t), 31.80(t), 48.51(t), 49.79(t), 69.27(t), 114.43(d), 123.91(s), 125.86(s), 127.42(d), 129.83(d), 153.18 (s) ppm.

Mass spectrum: m/e 317(M$^+$+, 0.11%), 318(M$^+$+1, 0.19%), 319(M$^+$+2, 0.07%), 142(100%), 44(88%).

Infrared absorption spectrum (liquid film method): max 2920$^s$, 2830$^s$, 1585$^w$, 1475$^s$, 1285$^s$, 1250$^s$, 1100$^m$, 800$^s$, 735$^s$ cm$^{-1}$.

Ultraviolet absorption spectrum (ethanol): max 204(30,300), 231(8,300), 285(2,000), 293 (1,770)nm.

Elementary analysis, values as C$_{16}$H$_{25}$Cl$_2$NO: calculated values: C:60.38, H:7.92, N:4.40(%), found values: C:60.65, H:7.83, N:4.52(%).

EXAMPLE 2

Synthesis of
N-2-(3,4-dichlorophenoxy)ethyl-N-n-octylamine
(compound No. 45)

In 20 ml of ethanol was dissolved 2.06 g (7.63 millimoles) of 2-(3,4-dichlorophenoxy)ethyl bromide, and 1.06 g (10.0 millimoles) of anhydrous sodium carbonate and 3.48 g (27.0 millimoles) of n-octylamine were added to the solution. The mixture was heated and refluxed on an oil bath for 6 hours. After cooling, the reaction mixture was poured into 100 ml of water and extracted with 20 ml of chloroform three times.

The organic layer was dried over magnesium sulfate and the solvent was removed by distillation, and the residue was purified by silica gel column chromatography (eluent: hexane/ethyl acetate/ethanol=70/26.5/3.5) to give 1.97 g (82% yield) of compound No. 45 in the form of a colorless oil.

The physical properties of the obtained compound were as follows.

$^{13}$C-NMR (CDCl$_3$): 14.03(q), 22.62(t), 27.32(t), 29.24(t), 29.48(t), 30.15(t), 31.80(t), 48.57(t), 49.88(t), 68.21(t), 114.43(d), 116.44(d), 123.97(s), 130.50(d), 132.72(s), 157.85(s) ppm.

Mass spectrum: m/e 317(M$^+$, 3.3%), 318(M$^+$+1, 1.1%), (319(M$^+$+2, 1.8%) 142(100%), 44(66%).

Infrared absorption spectrum (liquid film): max 2920$^{vs}$, 2850$^s$, 1595$^s$, 1565$^m$, 1455$^{vs}$, 1280$^s$, 1225$^s$, 1120$^s$, 1035$^s$, 1020$^m$ cm$^{-1}$.

Ultraviolet absorption spectrum (ethanol): max 204(31,700), 232(8,190), 284(1,700), 292(1,570)nm.

Elementary analysis, values as $C_{16}H_{15}Cl_2NO$: calculated values: C:60.38, H:7.92, N:4.40(%), found values: C:60.15, H:7.94, N:4.29(%).

EXAMPLE 3

Synthesis of N-2-pentachlorophenoxyethyl-N-n-octylamine (compound No. 60)

1) In 45 ml of dimethylformamide was dissolved 8.66 g (30.0 millimoles) of sodium pentachlorophenoxide, and 50 ml of dibromoethane was added to the solution and the mixture was heated at 100° C. for 8 hours.

The reaction mixture was poured into 250 ml of a saturated aqueous solution of sodium carbonate and extracted with chloroform, and the organic layer was washed with water and a saturated aqueous solution of sodium chloride, and dried over magnesium sulfate. The solvent was removed by distillation, and the obtained solids were washed sufficiently with methanol to give 3.58 g (32% yield) of 2-pentachlorophenoxyethyl bromide in the form of colorless solids.

The physical properties of the obtained compound were as follows:

Melting point: 71°–74° C.

$^1$H-NMR (CDCl$_3$) δ 3.64(t,J=6 Hz, 2H), 4.28(t,J=6 Hz, 2H)ppm.

2) In 20 ml of ethanol were dissolved 1.12 g (3.00 millimoles) of 2-pentachlorophenoxyethyl bromide prepared in 1) above and 1.29 g (10.0 millimoles) of n-octylamine, and 0.50 g of anhydrous sodium carbonate was added to the solution and the mixture was refluxed for 6 hours.

After cooling, the reaction mixture was poured into 100 ml of water and extracted with chloroform. The organic layer was dried over magnesium sulfate and the solvent was removed by distillation, and the residue was purified by silica gel column chromatography (eluent: hexane/ethyl acetate/ethanol=70/29/1) to give 0.91 g (71% yield) of compound No. 60 in the form of a colorless oil.

The physical properties of the obtained compound were as follows.

Infrared absorption spectrum (liquid film): λmax 213(87,000), 226$^{sh}$(20,500), 238$^{sh}$(10,300), 291$^{sh}$(540), 296(670)nm.

Elementary analysis values as $C_{16}H_{22}Cl_5NO$: calculated values: C:45.58, H:5.26, H:3.32(%), found values: C:46.68, H:5.19, N:3.18(%).

EXAMPLE 4

Synthesis of compound No. 68

In 40 ml of ether was gradually dissolved 3.18 g (10.0 millimoles) of N-2-(2,4-dichlorophenoxy)ethyl-N-n-octylamine (compound No. 22), and under ice cooling, slight excess of hydrochloric acid gas was blown into the solution to form crystals.

The formed crystals were collected by filtration and washed sufficiently with dry ether to give 3.47 g (98% yield) of compound No. 68 in the form of a white solid (having a melting point of 164° to 168° C.).

EXAMPLE 5

Synthesis of compound No. 83

In 40 ml of ethanol was dissolved 3.18 g (10.0 millimoles) of N-2-(2,4-dichlorophenoxy)ethyl-N-n-octylamine (compound No. 22), and under ice cooling, 1.27 g (11.0 millimoles) of 85% phosphoric acid was added to the solution to form crystals. The formed crystals were collected by filtration, washed sufficiently with ether and dried to give 4.02 g (98% yield) of compound No. 83 in the form of a white solid (having a melting point of 115° to 116° C.).

PREPARATION EXAMPLE 1 (WETTABLE POWDER)

| Component | Amount (parts by weight) |
|---|---|
| Compound No. 22 | 20 |
| Lignin-sulfonic acid | 3 |
| Polyoxyethylene alkylaryl ether | 2 |
| Diatomaceous earth | 75 |

The foregoing components were homogeneously mixed to give a wettable powder comprising 20% by weight of the active ingredient.

PREPARATION EXAMPLE 2 (POWDER)

| Component | Amount (parts by weight) |
|---|---|
| Compound No. 22 | 3 |
| Calcium stearate | 1 |
| Silica powder | 1 |
| Clay | 48 |
| Talc | 47 |

The foregoing components were homogeneously mixed to give a powder comprising 3% by weight of the active ingredient.

PREPARATION EXAMPLE 3 (WETTABLE POWDER)

| Component | Amount (parts by weight) |
|---|---|
| Compound No. 68 | 20 |
| Lignin-sulfonic acid | 3 |
| Polyoxyethylene alkylaryl ether | 2 |
| Diatomaceous earth | 75 |

The foregoing components were homogeneously mixed to give a wettable powder comprising 20% by weight of the active ingredient.

PREPARATION EXAMPLE 4 (POWDER)

| Component | Amount (parts by weight) |
|---|---|
| Compound No. 68 | 3 |
| Calcium stearate | 1 |
| Silica powder | 1 |
| Clay | 48 |
| Talc | 47 |

The foregoing components were homogeneously mixed to give a powder comprising 3% by weight of the active ingredient.

Test 1 (Antibacterial Test to Phyto-Pathogenic Bacteria

Antibacterial actions of the phenoxyalkylamine and phenoxyalkylamine salt to various phyto-pathogenic bacteria were examined.

More specifically, the bacterium causing black spot of cabbage, *Xanthomonas campestris pv. campestris*, the bacterium causing citrus canker, *S. campestris pv. citri*, the bacterium causing bacterial leaf blight of rice, *X. campestris pv. oryzae*, and the bacterium causing tomato canker, *Clavibacter michiganensis subs michiganensis,* were used and the action of inhibiting the growth of the bacterium on an agar plate was examined.

A test compound was added to a peptone-added potato extract medium, and a progressive 2-times dilution system having a maximum concentration of 100 ppm was prepared and the culture medium was cast into a Petri dish to form an agar plate.

The agar plate was inoculated with the bacterium to be tested and incubation was carried out at 28° C. for 2 days, and the growth of the bacterium was checked.

The obtained results are shown in Table 3.

The compounds of the present invention showed a strong antibacterial activity to all of the pathogenic bacteria employed.

TABLE 3

Results of Antibacterial Tests on Phyto-Pathogenic Bacteria
Minimum Growth Inhibition Concentration (ppm)

| Compound NO. | Xc | Xi | Xo | Cm |
|---|---|---|---|---|
| 3 | 12.5 | 12.5 | 3.2 | 6.3 |
| 4 | 12.5 | 12.5 | 3.2 | 6.3 |
| 12 | 12.5 | 12.5 | 3.2 | 12.5 |
| 13 | 12.5 | 12.5 | 3.2 | 12.5 |
| 14 | 6.3 | 6.3 | 1.6 | 6.3 |
| 17 | 6.3 | 12.5 | 3.2 | 6.3 |
| 18 | 6.3 | 12.5 | 1.6 | 3.2 |
| 19 | 6.3 | 12.5 | 3.2 | 3.2 |
| 22 | 6.3 | 6.3 | 3.2 | 3.2 |
| 23 | 6.3 | 12.5 | 6.3 | 3.2 |
| 24 | 12.5 | 12.5 | 6.3 | 6.3 |
| 35 | 12.5 | 25 | 6.3 | 12.5 |
| 36 | 12.5 | 25 | 6.3 | 6.3 |
| 40 | 12.5 | 12.5 | 6.3 | 6.3 |
| 41 | 12.5 | 12.5 | 6.3 | 3.2 |
| 44 | 12.5 | 12.5 | 6.3 | 12.5 |
| 45 | 6.3 | 12.5 | 6.3 | 6.3 |
| 46 | 6.3 | 12.5 | 6.3 | 3.2 |
| 49 | 6.3 | 25 | 3.2 | 6.3 |
| 50 | 12.5 | 12.5 | 3.2 | 3.2 |
| 52 | 12.5 | 12.5 | 6.3 | 3.2 |
| 53 | 6.3 | 6.3 | 1.6 | 1.6 |
| 65 | 6.3 | 6.3 | 1.6 | 3.2 |
| 67 | 6.3 | 6.3 | 3.2 | 6.3 |
| 68 | 6.3 | 6.3 | 1.6 | 3.2 |
| 69 | 6.3 | 6.3 | 1.6 | 3.2 |
| 71 | 6.3 | 6.3 | 1.6 | 3.2 |
| 72 | 6.3 | 6.3 | 1.6 | 3.2 |
| 74 | 6.3 | 6.3 | 1.6 | 6.3 |
| 78 | 6.3 | 6.3 | 1.6 | 3.2 |
| Streptomycin* | 25 | 25 | 6.3 | 6.3 |

Note
*commercially available comparative agent
Xc: *X. campestris* pv. campestris
Xi: *X. campestris* pv. citri
Xo: *X. campestris* pv. oryzae
Cm: *Clavibacter michiganensis* subs. *michiganensis*

Table 2 (Test of Preventing Citrus Canker)

Leaf pieces of ca. 1 cm large were cut out from summer orange leaves and immersed in a test solution at a predetermined concentration for 20 minutes. The leaf pieces were taken out from the test solution and air-dried. Then, they were inoculated with a suspension of cells of the bacterium causing citrus canker (about $10^8$ cells per ml) by using a needle.

The inoculated leaf pieces were placed in a Petri dish on which a wet filter paper was put, and incubation was carried out at 28° C. for 10 days and the outbreak of the disease was checked. The disease attack ratio was calculated according to the following formula:

$$\text{Disease attack ratio (\%)} = \frac{0 \times n_0 + 1 \times n_1 + 2 \times n_2 + 3 \times n_3}{3 \times N} \times 100$$

wherein $n_0$ represents the number of leaf pieces having a disease severity index of 0 (no disease), $n_1$ represents the number of leaf pieces having a disease severity index of 1 (slight disease), $n_2$ represents the number of leaf pieces having a disease severity index of 2 (medium disease), $n_3$ represents the number of leaf pieces having a disease severity index of 3 (violent disease), and N represents the total number of the examined leaf pieces.

Furthermore, the degree of phytotoxicity was visually examined.

The obtained results are shown in Tables 4-(1) and 4-(2).

TABLE 4-(1)

Results of Test of Preventing Citrus Canker (Phenoxyalkylamines)

| Compound No. | Concentration (ppm) | Disease Attack Ratio (%) | Phytotoxicity** |
|---|---|---|---|
| 4 | 300 | 13.3 | — |
| 12 | 300 | 23.8 | — |
| 13 | 300 | 20.8 | — |
| 14 | 300 | 14.3 | — |
| 17 | 300 | 16.7 | — |
| 18 | 300 | 26.7 | — |
| 22 | 300 | 14.3 | — |
| 41 | 300 | 22.2 | — |
| 44 | 300 | 20.0 | — |
| untreated | | 50.0 | — |
| cocide* (wettable powder) | 200 times dilution | 26.7 | — |

Note
*commercially available comparative agent
**"—" indicates no phytotoxicity (the same will apply hereinafter)

TABLE 4-(2)

Results of Test of Preventing Citrus Canker (Phenoxyalkylamines Salts)

| Compound No. | Concentration (ppm) | Disease Attack Ratio (%) | Phytotoxicity** |
|---|---|---|---|
| 65 | 300 | 13.3 | — |
| 67 | 300 | 10.0 | — |
| 68 | 300 | 0.0 | — |
| 69 | 300 | 13.3 | — |
| 71 | 300 | 10.0 | — |
| 72 | 300 | 16.7 | — |
| 74 | 300 | 16.7 | — |
| 78 | 300 | 13.3 | — |
| untreated | | 66.7 | — |
| cocide* (wettable powder) | 200 times dilution | 16.7 | ± |

Note
*commercially available
**"±" indicates slight phytotoxicity

Test 3 (Test of Preventing Bacterial Leaf Blight of Rice)

An aqueous solution containing a test compound at a predetermined concentration was spread to rice plants of the 5-leaf stage (variety: Koshihikari) grown in a pot having a diameter of 6 cm. After one day, the rice plants were shear-inoculated with a cell suspension of the bacterium causing bacterial leaf blight of rice, which had a concentration of $10^8$ cells per ml.

When 3 weeks passed from the inoculation, the lengths of lesions were measured, and the control values were calculated according to the following formula:

$$\text{Control value (\%)} = \left(1 - \frac{\text{average leaf length in treated zone}}{\text{average leaf length in untreated zone}}\right) \times 100$$

The obtained results are shown in Table 5.

TABLE 5

Results of Test of Preventing Bacteria Leaf Blight of Rice

| Compound No. | Concentration (ppm) | Control Value (%) | Phytotoxicity |
|---|---|---|---|
| 9 | 500 | 80.5 | — |
| 13 | 500 | 90.0 | — |
| 17 | 500 | 95.1 | — |
| 22 | 500 | 88.2 | — |
| 34 | 500 | 83.7 | — |
| 35 | 500 | 96.3 | — |
| 49 | 500 | 75.6 | — |
| Phenazine* (wettable powder) | 500 times dilution | 60.1 | — |

Note
*commercially available comparative agent

Test 4 (Test of Preventing Dry Rot)

Radish disks of 2 cm in diameter and 1 cm thickness were prepared and immersed in an aqueous solution containing a test compound at a predetermined concentration for 1 hour.

The radish disks were taken out from the test solution and air-dried. A bacterium suspension was dropped on central portions of the disks and the disks were maintained at 28° C. for 24 hours. The disease attack degree was examined and the control values were calculated according to the following formula:

$$\text{Control value (\%)} = \left(1 - \frac{\text{number of rotted disks}}{\text{number of examined disks}}\right) \times 100$$

The obtained results are shown in Tables 6-(1) and 6-(2).

TABLE 6-(1)

Results of Test Preventing Dry Rot (Phenoxyalkylamines)

| Compound No. | Concentration (ppm) | Control Value (%) | Phytotoxicity |
|---|---|---|---|
| 17 | 400 | 100 | — |
| 18 | 400 | 90 | — |
| 44 | 400 | 100 | — |
| 45 | 400 | 90 | — |
| cocide* (wettable powder) | 2000 times dilution | 80 | — |

Note
*commercially available comparative agent

TABLE 6-(2)

Results of Test Preventing Soft Rot (Phenoxyalkylamines)

| Compound No. | Concentration (ppm) | Control Value (%) | Phytotoxicity |
|---|---|---|---|
| 65 | 400 | 90 | — |
| 67 | 400 | 90 | — |
| 68 | 400 | 100 | — |
| 69 | 400 | 80 | — |
| 71 | 400 | 90 | — |
| 72 | 400 | 90 | — |
| 74 | 400 | 90 | — |
| 78 | 400 | 90 | — |
| cocide* (wettable powder) | 1000 times dilution | 80 | — |

Note
*commercially available comparative agent

Test 5 (Test of Stability to Ultraviolet Light)

A watch glass was charged with 0.5 ml of a methanol solution containing 2% by weight of compound No. 68, and the watch glass was air-dried.

The watch glass was placed 20 cm below a sterilizing lamp (10W) and irradiated for a predetermined time.

Then, 0.5 ml of methanol was added into the watch glass to form a solution, and the minimum growth inhibition concentration was measured.

The obtained results are shown in Table 7.

From the results shown in Table 7, it is seen that in case of compound No. 22, the minimum inhibition concentration drastically increased after 3 days' irradiation, and compound No. 22 was stable during 2 days' irradiation. In contrast, the minimum inhibition concentration was not changed even after 7 days' irradiation by the sterilizing lamp in case of compound No. 68, and it was confirmed that compound No. 68 was more stable to ultraviolet light.

TABLE 7

Results of Test of Stability to Ultraviolet Light

| Compound No. | Number of Days of Irradiation by Stabilizing Lamp | | | | |
|---|---|---|---|---|---|
| | 1 | 2 | 3 | 4 | 7 |
| 22 | 6.3 | 6.3 | 12.5 | 12.5 | 12.5 |
| 68 | 6.3 | 6.3 | 6.3 | 6.3 | 6.3 |

Note

Each value under the number in the table indicates the minimum growth inhibition concentration (ppm) to the bacterium causing citrus canker.

Test 6 (Phytotoxicity Test)

Compound No. 68 was dissolved at a predetermined concentration, and this solution was sprayed to plants of the 3-leaf stage. After 1 week, the phytotoxicity was examined.

Rice, wheat, tomato and cucumber were used as the test plant.

The obtained results are shown in Table 8.

In case of compound No. 22, the phytotoxicity was observed at a high concentration of 1,000 ppm.

In contrast, compound No. 68 did not show any phytotoxicity to any of the plants even at a high concentration of 1,000 ppm.

TABLE 8

| Compound No. | Results of Phytotoxicity Test Phytotoxicity | | | |
|---|---|---|---|---|
| | rice | wheat | tomato | cucumber |
| 22 | + | + | + | + |

TABLE 8-continued

| Compound | Results of Phytotoxicity Test Phytotoxicity | | | |
|---|---|---|---|---|
| No. | rice | wheat | tomato | cucumber |
| 68 | — | — | — | — |

We claim:

1. A method of preventing or curing citrus canker, bacterial leaf blight of rice, bacterial shot hole of peach, black rot of cabbage, bacterial blight of lettuce, bacterial spot of melon, leaf blight of soy bean, tomato canker and soft rot of Chinese cabbage which comprises applying a horticultural or bactericidal composition directly to a plant being treated or to soil or water used to culture the plant, wherein the horticultural or bactericidal composition comprises as an active ingredient a compound comprising at least one member selected from the group consisting of phenoxyalkylamines represented by formula I and salts of said phenoxyalkylamines represented by formula II:

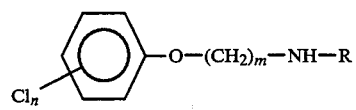

I

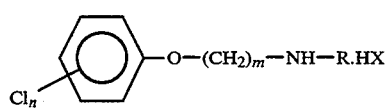

II wherein R represents a straight saturated hydrocarbon having 8 to 12 carbon atoms, n is an integer of from 1 to 5, m is an integer of from 2 to 4, and HX represents a mineral acid.

2. A method for killing plant pathogenic bacteria belonging to *Xanthomonas campestris*, *Clavibacter michiganensis* or *Erwinia carotovora* which comprises applying to a plant infected with the bacteria or to the soil or water used to culture the plant at least one compound selected from the group consisting of compounds having the following general formulae

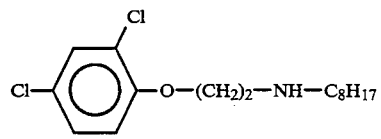

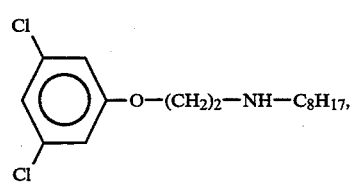

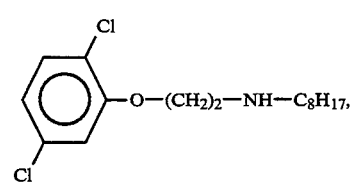

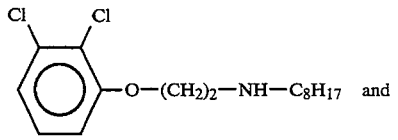

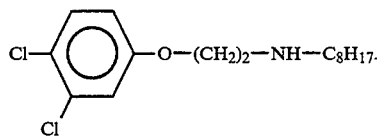

3. The method for killing plant pathogenic bacteria according to claim 2 wherein the active ingredient of the composition is represented by the following formula:

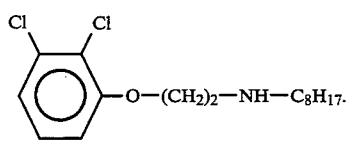

4. A method for preventing or curing citrus canker, bacterial leaf blight of rice, bacterial shot hole of peach, black rot of cabbage, bacterial blight of lettuce, bacterial spot of melon, leaf blight of soy bean, tomato canker or soft rot of Chinese cabbage, which comprises applying a compound directly to a plant to be treated or to soil or water used to culture the plant, wherein the compound is at least one phenoxyalkylamine selected from the group consisting of phenoxyalkylamines represented by the following formulae

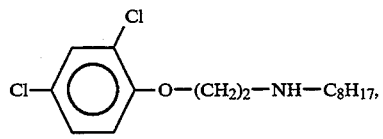

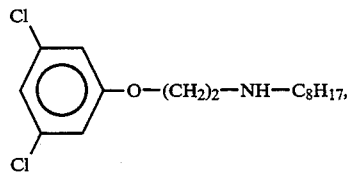

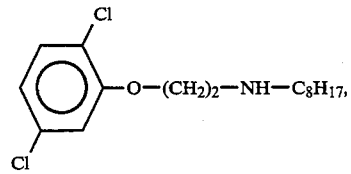

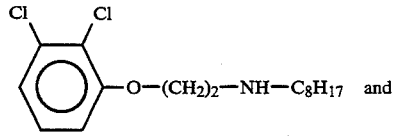

-continued

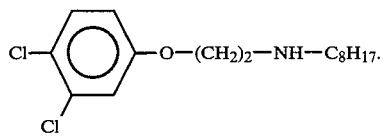

5. A method for killing plant pathogenic bacteria belonging to the group consisting of *Xanthomonas campestris, Clavibarcer michiganensis* and *Erwinia carotovora* which comprises applying an agent directly to a plant to be treated or to soil or water used to culture the plant, wherein the agent comprises as an active ingredient a phenoxyalkylamine represented by formula (I) or a salt of said phenoxyalkylamine represented by formula (II):

(I)

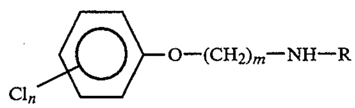

-continued (II)

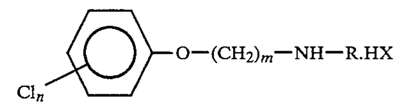

wherein R represents a straight saturated hydrocarbon having 8 or 9 carbon atoms, n is an integer of from 1 to 5, m is an integer of from 2 to 4, and HX represents a mineral acid.

6. The method of claim 1 wherein R in formula I and formula II represents $C_8H_{17}$ and HX in formula II is HCl.

7. The method of claim 1 which comprises applying the composition in the form of a powder in an amount of about 2-6 kg per 10 acres.

8. The method of claim 1 which comprises applying to the composition in the form of a wettable powder, liquid, or emulsifiable concentrate containing about 20% by weight active ingredient diluted to contain 0.05 to 3 kg of active ingredient per 100 to 500 liters of water, per about 100 ares.

* * * * *